(12) United States Patent
Kitani et al.

(10) Patent No.: US 7,963,951 B2
(45) Date of Patent: Jun. 21, 2011

(54) MEDICAL VALVE DEVICE

(75) Inventors: Ichiro Kitani, Fukuroi (JP); Yoshihiro Wada, Fukuroi (JP); Takuya Fujimine, Fukuroi (JP)

(73) Assignee: Tyco Healthcare Group LP, Mansfield, MA (US)

(*) Notice: Subject to any disclaimer, the term of this patent is extended or adjusted under 35 U.S.C. 154(b) by 1140 days.

(21) Appl. No.: 11/673,090

(22) Filed: Feb. 9, 2007

(65) Prior Publication Data

US 2008/0195031 A1    Aug. 14, 2008

(51) Int. Cl.
*A61M 5/00* (2006.01)
*A61M 5/178* (2006.01)
*A01G 25/16* (2006.01)

(52) U.S. Cl. .............. 604/248; 604/167.05; 137/625

(58) Field of Classification Search .......... 604/4.01, 604/6.1, 167.05, 236, 248, 288.03; 137/625; 251/309
See application file for complete search history.

(56) References Cited

U.S. PATENT DOCUMENTS

| | | | | |
|---|---|---|---|---|
| 4,207,923 A | * | 6/1980 | Giurtino | 137/625.47 |
| 5,046,528 A | * | 9/1991 | Manska | 137/556 |
| 5,156,186 A | * | 10/1992 | Manska | 137/556 |
| 5,443,453 A | * | 8/1995 | Walker et al. | 604/248 |
| 5,578,016 A | * | 11/1996 | Zinger | 604/248 |
| 5,832,959 A | * | 11/1998 | Szymczakowski et al. | 137/625.47 |
| 5,865,812 A | * | 2/1999 | Correia | 604/248 |
| 5,882,348 A | * | 3/1999 | Winterton et al. | 604/537 |
| 7,232,428 B1 | * | 6/2007 | Inukai et al. | 604/248 |
| 7,614,857 B2 | * | 11/2009 | Fuechslin et al. | 417/519 |
| 7,695,445 B2 | * | 4/2010 | Yuki | 604/4.01 |
| 2002/0084437 A1 | * | 7/2002 | Nitsche et al. | 251/309 |

FOREIGN PATENT DOCUMENTS

| | | |
|---|---|---|
| EP | 1459783 A1 | 9/2004 |
| JP | 11-342209 | 12/1999 |
| JP | 2003-159336 | 6/2003 |
| WO | 2004/101061 A1 | 11/2004 |
| WO | 2004/039446 A1 | 7/2007 |

OTHER PUBLICATIONS

Extended European Search Report for Application No. 06023657.7-2310 dated Apr. 5, 2007.

* cited by examiner

*Primary Examiner* — Nicholas D Lucchesi
*Assistant Examiner* — Victoria P Campbell
(74) *Attorney, Agent, or Firm* — Lisa E. Winsor, Esq.

(57) ABSTRACT

A medical valve device includes a valve unit. The valve unit includes two fluid channels and is positionable to selectably connect two inlet ports and an outlet port such that in one position, fluid introduced at a first inlet port is caused to flow in a first fluid channel to a second inlet port and thence in a second fluid channel from said second inlet port to said outlet port.

11 Claims, 11 Drawing Sheets

MEDICAL VALVE DEVICE

FIELD OF THE INVENTION

The present invention generally relates to a medical valve device.

BACKGROUND OF THE INVENTION

A stopcock for medical treatment is mounted at several tubes being used in medical treatment, especially liquid transfer, blood transfer, and artificial dialysis, and switches the communication and the cut off of each tube for medical treatment. In a representative three-way stopcock as such a stopcock for medical treatment, three tubes for medical treatment are mounted, and the communication and the cut off of each tube for medical treatment are switched. In general, the three-way stopcock has two inflow ports and one outflow port and is used to switch the communication and the cut off of the inflow ports and the outflow port.

The three-way stopcock is used in joining a mixture injection channel to a main flow channel and temporarily or always mixing another liquid such as liquid medicine from the mixture injection channel with a liquid such as liquid medicine flowing in the main flow channel. In this case, one inflow port and the outflow port formed in the three-way stopcock are linearly formed to form the main flow channel, and the other inflow port is installed so that it can perpendicularly or obliquely cross the main flow channel. The other inflow port is also used as the mixture injection channel.

The three-way stopcock is generally equipped with a main body and a stopcock. The main body consists of a tubular part having a cylindrical center space and three branch tube parts mounted with separation at an angle interval of 90° on the outer peripheral surface of the tubular part. The stopcock includes a columnar valve rotatably mounted in the cylindrical space formed at the center of the tubular part of the main body and a grip part connected to the end of the valve and to rotate the valve in the cylindrical space. Also, a communication flow channel wherein branch flow channels formed in each branch tube of the main body can communicate with other branch flow channels is formed in the valve. Then, with rotation of the valve in the cylindrical space, the communication and the cut off of each branch flow channel are carried out via the communication flow channel formed in the valve. Since a tube for medical treatment is mounted in each branch tube, the communication and the cut off of the tubes for medical treatment are switched by rotation of the valve.

In this three-way stopcock, recently, various investigations have been proposed in which the workability, etc., are considered. For example, in the technique described in patent publication 1, the communication flow channel formed in the valve of the three-way stopcock has a circular arc shape, three vertical channels are installed at an interval of 90° in the circular arc shaped channel, and these three vertical channels as the branch flow channels of the main body can communicate with each other. According to Japanese Kokai Patent Application No. 2003 159336, since the communication flow channel has a circular arc shape, the dead space as an internal space in which a liquid or gas remains in the valve is reduced and the liquid flowing in the inside can be smoothly circulated. Also, since the branch flow channels do not directly communicate with the circular arc shaped channel but are connected to the vertical channels connected to the circular arc shaped channel, the flow channel can be cut off by slight rotation of the valve, so that the workability is improved.

On the other hand, if the mixture injection channel is connected to the main flow channel using a three-way stopcock, and liquid medicine is mixed into the main flow channel from the mixture injection channel, the space in the flow channel for forming the mixture injection channel is irrelevant to the flow of the main flow channel and is dead space. Therefore, liquid from the mixture injection channel remains in this part. Also, air bubbles remain in the space in the flow channel for forming the mixture injection channel. It is preferable to greatly reduce the retention of liquid and air bubbles in terms of workability, etc.

In the three-way stopcock described in the above mentioned patent publication JP 2003 159336, since the communication flow channel formed in the valve has a circular arc shape, the dead space in the branch flow channel for forming the mixture injection channel is not necessarily reduced, although the dead space in the valve can be reduced. Therefore, liquid medicine and air bubbles are likely to remain in this part.

SUMMARY OF THE INVENTION

In one aspect of the present invention, a medical valve device generally comprises a main body and first, second and third connection ports attached to the main body. A valve unit is rotatable in the main body for selectably connecting the connection ports together in fluid flow communication. The valve unit is shaped to provide a first fluid flow channel and a second fluid flow channel. The valve unit is positionable in the main body in a first state such that the first fluid flow channel provides a fluid flow connection between the first port and the third port but not the second port and the second fluid flow channel provides a fluid flow connection between the second port and the third port but not the first port. The valve unit is also positionable in the main body in a second state such that the first flow channel provides a fluid flow connection between the third port and the second port but not the first port and no fluid flow connection is provided to the first port. The valve unit is further positionable in the main body in a third state such that the second flow channel provides a fluid flow connection between the first port and the third port but not the second port and no fluid flow connection is provided to the second port.

In another aspect, a stopcock for medical treatment generally comprises a tubular part having an inner wall. A main body includes a first branch flow channel with a first opening part opening into the inner wall and formed from the first opening part toward the outside of the tubular part. A second branch flow channel has a second opening part opening in the inner wall and is formed from the second opening part toward the outside of the tubular part. A third branch flow channel has a third opening part opening in the inner wall and is formed from the third opening part toward the outside of the tubular part. A valve is mounted at the inner periphery of the tubular part that can be rotated around the axis of the tubular part to switch the communication and the cut off of the first branch flow channel, the second branch flow channel, and the third branch flow channel by rotating. The valve generally comprises a first communication flow channel that can communicate with the first branch flow channel and the third branch flow channel. A second communication flow channel can communicate with both the second branch flow channel and the third branch flow channel. The valve is configured to adopt a state in which the communication with the first branch flow channel is cut off when the first communication flow channel communicates with both the first branch flow channel and the third branch flow channel while communication with the second branch flow channel is cut off. The communication in the valve is cut off in the first communication flow channel and the second communication flow channel.

In another aspect, a stopcock for medical treatment generally comprises a tubular part having an inner wall. A main body includes a first branch flow channel with a first opening part opening in the inner wall. The first branch flow channel is formed from the first opening part toward the outside of the tubular part. A second branch flow channel has a second opening part opening in the inner wall and is formed from the second opening part toward the outside of the tubular part. A third branch flow channel has a third opening part opening in the inner wall and is formed from the third opening part toward the outside of the tubular part. A valve is mounted at the inner periphery of the tubular part. The valve is configured for rotation around the axis of the tubular part and for switching the communication and the cut off of the first branch flow channel, the second branch flow channel, and the third branch flow channel by rotating the valve. The valve comprises a first channel section formed in the peripheral direction at the outer periphery of the valve such that the first branch flow channel and the third branch flow channel can communicate with each other. A second channel section is formed parallel to the first channel section in the peripheral direction at the outer periphery of the valve such that the second branch flow channel and the third branch flow channel can communicate with each other. A partition part is formed between the first channel section and the second channel section to cut off the communication of the first channel section and the second channel section in the valve.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1:
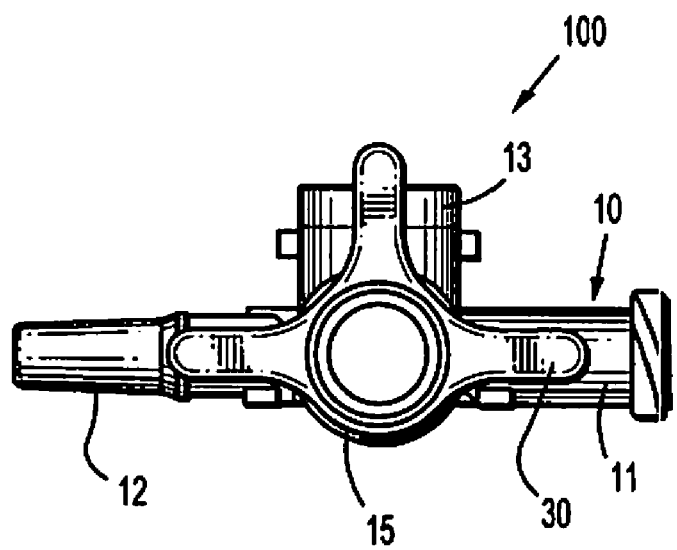
FIG. 1 is a plan view showing the stopcock for medical treatment of an embodiment of the present invention.
Figure 2:
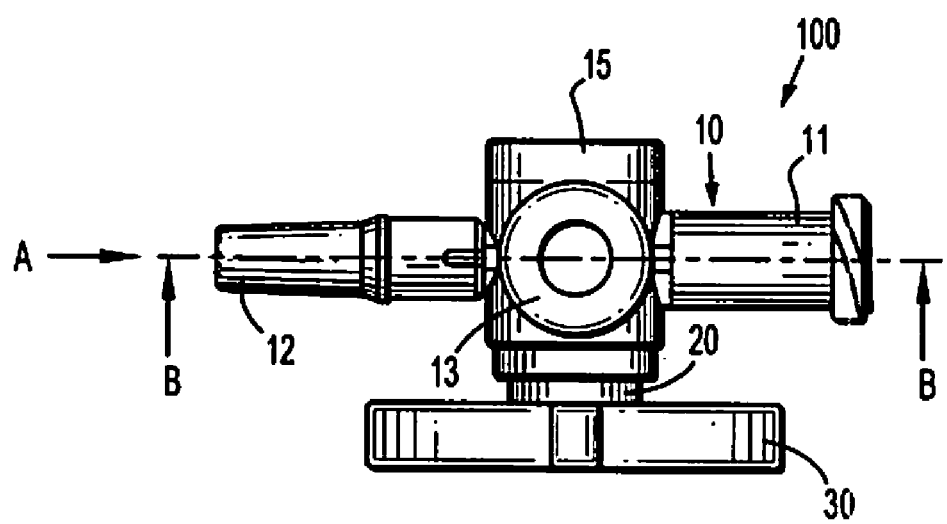
FIG. 2 is a front view showing the stopcock for medical treatment of said embodiment of the present invention.
Figure 3:
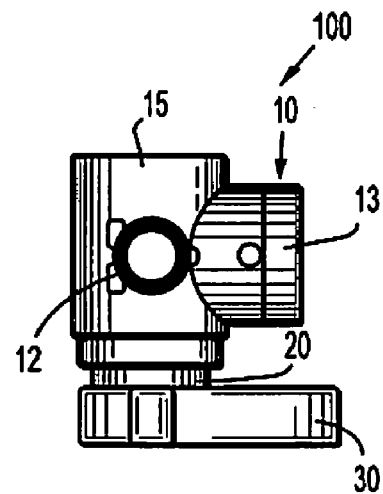
FIG. 3 is a diagram in the arrow A direction in FIG. 2.

Embodiments of the stopcock for medical treatment of the present invention are now explained in detail. FIG. 1 is a plan view showing a three way stopcock as the stopcock for medical treatment of this embodiment, FIG. 2 is a front view, and FIG. 3 is a diagram in the direction of arrow A in FIG. 2. As shown in the figures, a three way stopcock 100 is equipped with a main body 10, a valve 20, and a grip part 30. The valve 20 and the grip 30 are formed in a body, and the valve 20 is mounted in the main body 10.

As is especially well shown in FIG. 2, the main body 10 consists of a tubular part 15 and first branch tube 11, second branch tube 12, and third branch tube 13 as three branch tubes mounted in the tubular part 15. Also, as the material of the main body 10, polycarbonate (PC), polypropylene (PP), or polyethylene terephthalate (PET) can be selected; however the material is not limited to these.

Figure 4:
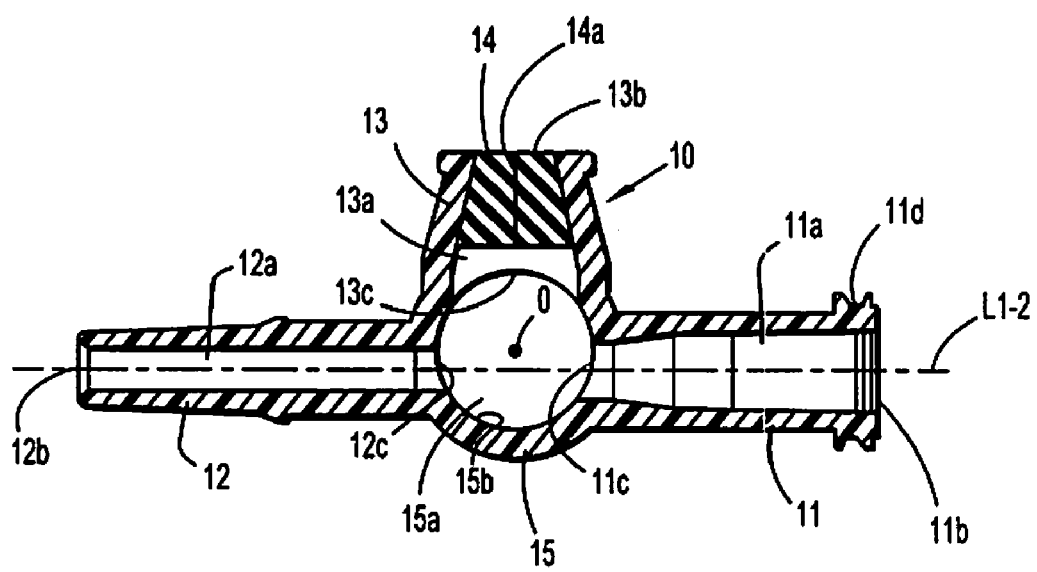
FIG. 4 is a cross section of only the main body of the B-B cross section in FIG. 2.

FIG. 4 is a cross section of only the main body 10 along the line B-B in FIG. 2. As can be seen from FIG. 4, in the tubular part 15, a cylindrical space 15a with a circular cross section and in the shape of a cylinder is formed at its inner periphery. Then, the first branch tube 11 is connected to the right side of the tubular part 15 in the figure. The first branch tube 11 is a tubular part in which a first branch flow channel 11a is formed. At one end (the right end in the figure) of the first branch flow channel 11a, a first outer opening part 11b is formed toward the outside, and at the other end (the left end in the figure), a first inner opening part 11c is formed. The first inner opening part 11c opens in an inner wall 15b of the tubular part 15 for forming the cylindrical space 15a. Therefore, the first branch flow channel 11a is formed from the first inner opening part 11c toward the outside of the tubular part 15.

Also, the third branch tube 13 is connected from the upper side of the tubular part 15 in the figure. The third branch channel 13 is a tubular part in which a third branch flow channel 13a is formed. At one end (the upper end in the figure) of the third branch flow channel 13a, a third outer opening part 13b is formed toward the outside, and at the other end (the lower end in the figure), a third inner opening part 13c is formed by opening in the inner wall 15b of the tubular part 15. Therefore, the third branch flow channel 13a is formed from the third inner opening part 13c toward the outside of the tubular part 15.

Furthermore, the second branch tube 12 is connected to the left side of the tubular part 15 in the figure. The second branch tube 12 is a tubular part in which a second branch flow channel 12a is formed. At its one end (the left end in the figure), a second outer opening part 12b is formed toward the outside, and at its other end (the right end in the figure), a second inner opening part 12c is opened in the inner wall 15b of the tubular part 15. Therefore, the second branch flow channel 12a is formed from the second inner opening part 12c toward the outside of the tubular part 15.

As can be seen from FIG. 4, the first branch tube 11, second branch tube 12, and third branch tube 13 are respectively connected at intervals of about 90° to the tubular part 15. The first branch tube 11 and the second branch tube 12 are oppositely arranged while sandwiching the tubular part 15, and the first inner opening part 11c and the second inner opening part 12c almost face each other. Then, the first branch flow channel 11a and the second branch flow channel 12a are formed so that they have a common flow channel axis L1 2. The flow channel axis L1 2 coincides with the straight line that connects the center of the first inner opening part 11c and the center of the second inner opening part 12c.

Also, the third branch tube 13 is arranged at a position separated at an interval of 90° respectively from the first and second branch flow channels 11a and 12a in the peripheral direction of the tubular part 15. The third branch flow channel 13a is formed perpendicularly to axis L1 2. Also, the first inner opening part 11c, second inner opening part 12c, and third inner opening part 13c opening in the inner wall 15b of the tubular part 15 respectively have the same axial height position of the inner wall 15b and are formed at different positions in the peripheral direction.

The third branch tube 13 is shorter than the first branch tube 11 and the second branch tube 12 in the axial direction. It is formed short since the dead space in this part is decreased by reducing the flow channel area of the third branch flow channel 13a in the third branch tube 13. Also, the inner diameter of the third branch tube 13 is greater than the inner diameter of the first branch tube 11 and the second branch tube 12.

In the third branch tube 13, a seal member 14 is mounted. As the seal member 14, an elastic body such as a synthetic rubber material is used, and the seal member is used to cut off communication of the third branch flow channel 13a to the outside. Also, a slit 14a is formed in the seal member 14. The slit 14a is used as an insertion opening when the Luer part of a syringe, etc., is inserted into the third branch tube 13 and a liquid is fed from the Luer part.

Figure 5:
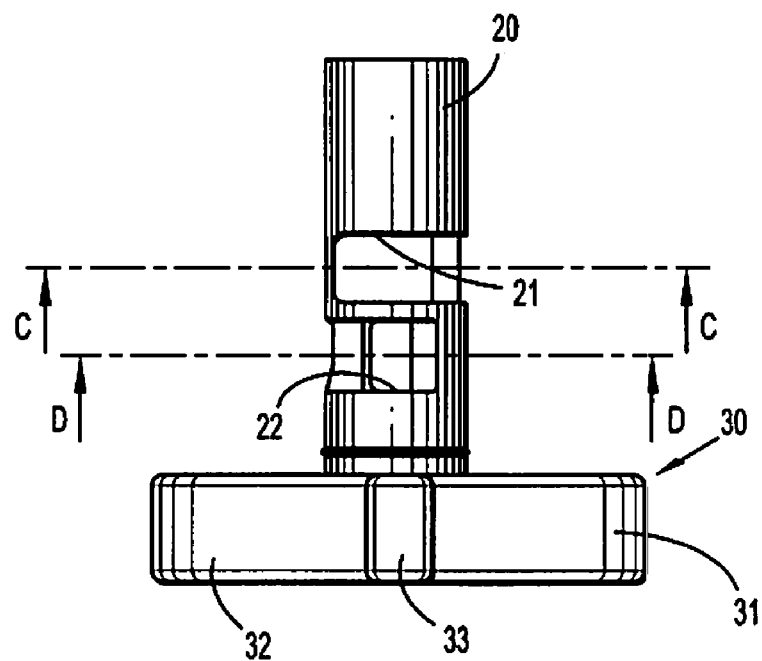
FIG. 5 is a front view showing the valve and grip part of the embodiment of the present invention.
Figure 6:
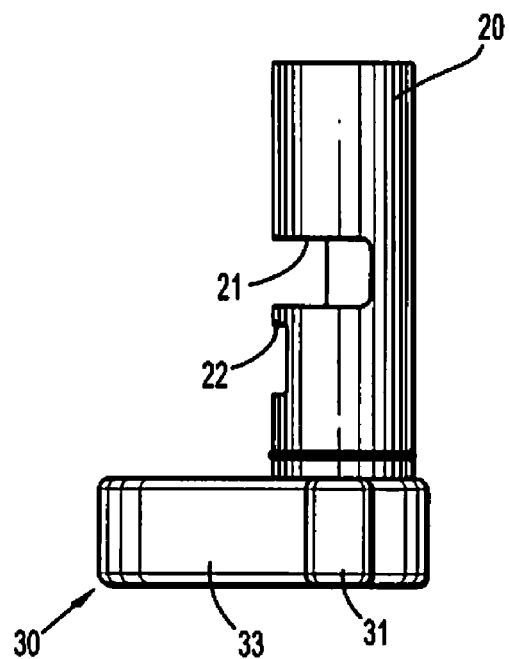
FIG. 6 is a right side view showing the valve and the grip part of the embodiment of the present invention.
Figure 7:
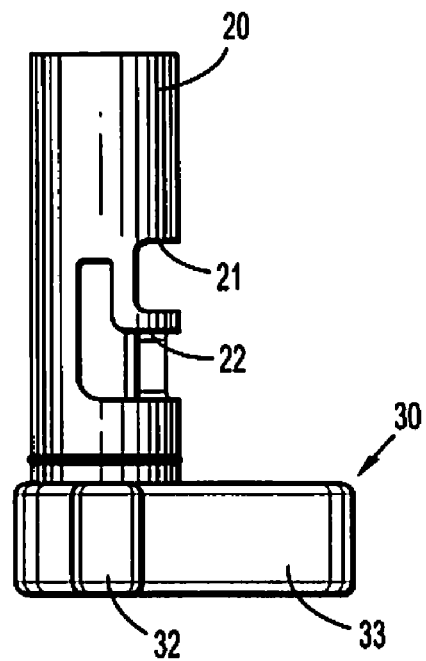
FIG. 7 is a left side view showing the valve and the grip part of the embodiment of the present invention.
Figure 8:
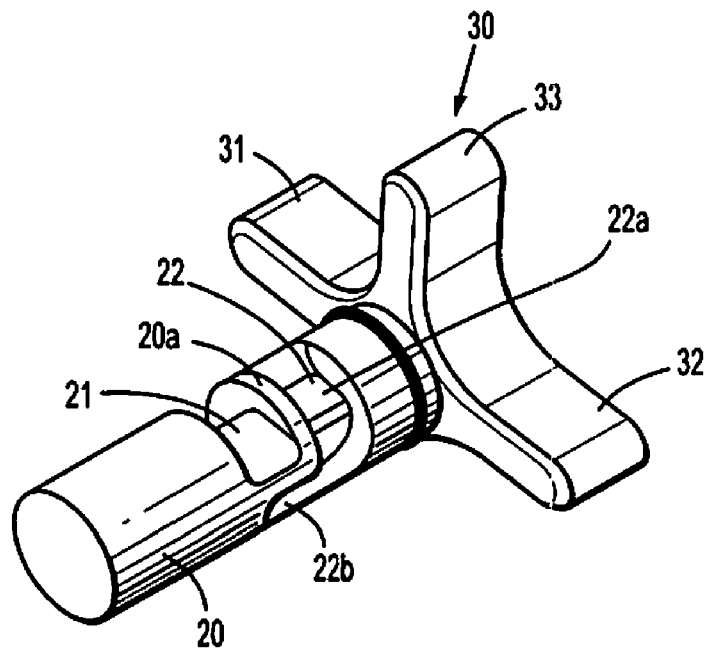
FIG. 8 is an oblique view showing the valve and the grip part of the embodiment of the present invention.

FIG. 5 is a front view showing the valve 20 and the grip part 30, FIG. 6 is a view of FIG. 5 observed from the right, FIG. 7 is a view of FIG. 5 observed from the left, and FIG. 8 is an oblique view. As shown in these figures, the grip part 30 is mounted at the end of the valve 20. The valve 20 is formed in an approximately columnar shape, and a first channel section 21 as a first communication flow channel and a second channel section 22 as a second communication flow channel are formed at its outer periphery. The grip 30 is equipped with three arms (first arm part 31, second arm part 32, and third arm part 33) extending radially outward from the base end of the valve 20. Each arm part is formed at an interval of 90° in the diameter directions of the valve 20, and the cross section of the three arm parts is approximately T-shaped.

Figure 9:
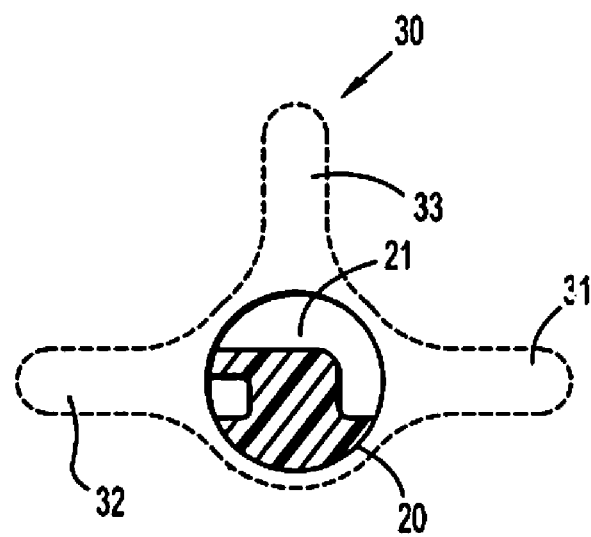
FIG. 9 shows a sectional shape of a first channel section in which the grip part observed from the same direction is added to the C-C cross section in FIG. 5.
Figure 10:
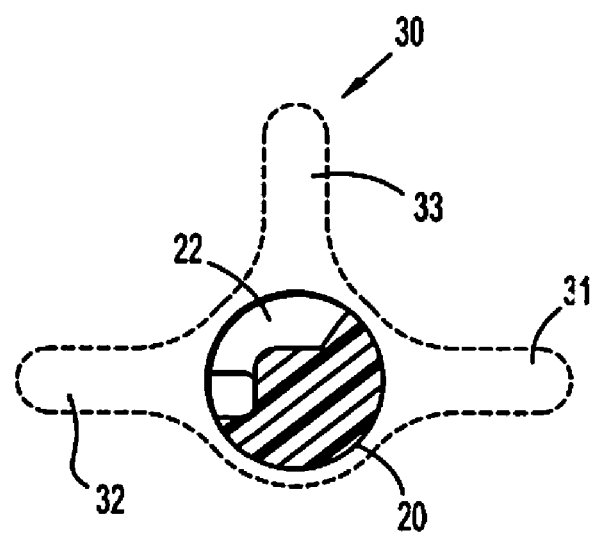
FIG. 10 shows a sectional shape of a second channel section in which the grip part observed from the same direction is added to the D-D cross section in FIG. 5.

FIG. 9 shows the sectional shape of the first channel section 21 formed in the valve 20 in which the grip part 30 observed from the same direction is added to the C C cross section in FIG. 5 by a dotted line. As can be seen from FIG. 9, the first channel section 21 is formed by notching the outer periphery of the valve 20 in a key shape in a range of about 180°, and in the figure, an area from the upper left side to the upper right side of the valve 20 is opened. Also, FIG. 10 shows a sectional shape of the second channel section 22 formed in the valve 20 in which the grip part 30 observed from the same direction is added to the D D cross section in FIG. 5 by a dotted line. As can be seen from FIG. 10, the second channel section 22 is formed by notching the outer periphery of the valve 20 in a range of about 120° in the peripheral direction. In the figure, an area from the left side to the upper right side of the outer periphery of the valve 20 is opened at the outer periphery of the valve 20.

Also, as can be seen from FIG. 8, the second channel section 22 has a peripheral channel part 22a notched in the peripheral direction of the valve 20 and an axial channel part 22b notched in the axial direction from the end of the peripheral channel part 22a. The first channel section 21 and the peripheral channel part 22a of the second channel section 22 are formed parallel to the peripheral direction of the valve 20. The axial channel part 22b of the second channel section 22 is formed in the axial direction of the valve 20 such that it can be wound into the first channel section 21 from the end of the peripheral channel part 22a. Then, the two channel sections 21 and 22 are hindered from communicating with each other in the valve 20 by the partition part 20a formed between the two channel sections 21 and 22.

Also, as can be seen from FIG. 9, the first arm part 31 of the grip part 30 extending in the right direction in the figure, that is, if indicated by the hand direction of a clock, in the direction of 3 o'clock. The right end of the first channel section 21 in the figure is opened in the 3 o'clock direction. On the other hand, as can be seen from FIG. 10, the second arm part 32 of the grip part 30 extends in the left direction in the figure, that is, if indicated by the hand direction of a clock, in the direction of 9 o'clock. The left end of the second channel section 22 in the figure is opened in the 9 o'clock direction. Also, the third arm part 33 of the grip part 30 extends in the upper direction in FIGS. 9 and 10, that is, that is, if indicated by the hand direction of a clock, in the direction of 12 o'clock. Also, as the material of the valve 20 and the grip part 30, polyethylene (PE), polyoxymethylene (POM), polypropylene (PP), etc., can be selected, but the material is not limited to these.

In the three way stopcock 100 in this embodiment, as mentioned above, the valve 20 is used by liquid tightly inserting it into the cylindrical space 15a formed in the tubular part 15 of the main body 10. The valve 20 is inserted into the cylindrical space 15a such that the first inner opening part 11c, second inner opening part 12c, and third inner opening part 13c formed in the main body 10 can face the axial position of the part in which the first channel section 21 and the second channel section 22 of the valve 20 are formed.

Also, as shown in FIG. 4, the center O of the cylindrical space 15a of the main body 10 is positioned in the figure higher than the common flow channel axis L1 2 of the first branch flow channel 11a and the second branch flow channel 12a. Since the rotation center of the valve 20 inserted into the cylindrical space 15a matches the center O of the cylindrical space 15a, the rotation center of the valve 20 is offset upward in the figure with respect to the flow channel axis L1-2, that is, the straight line that connects the center of the first inner opening part 11c and the center of the second inner opening part 12c.

Figure 11:
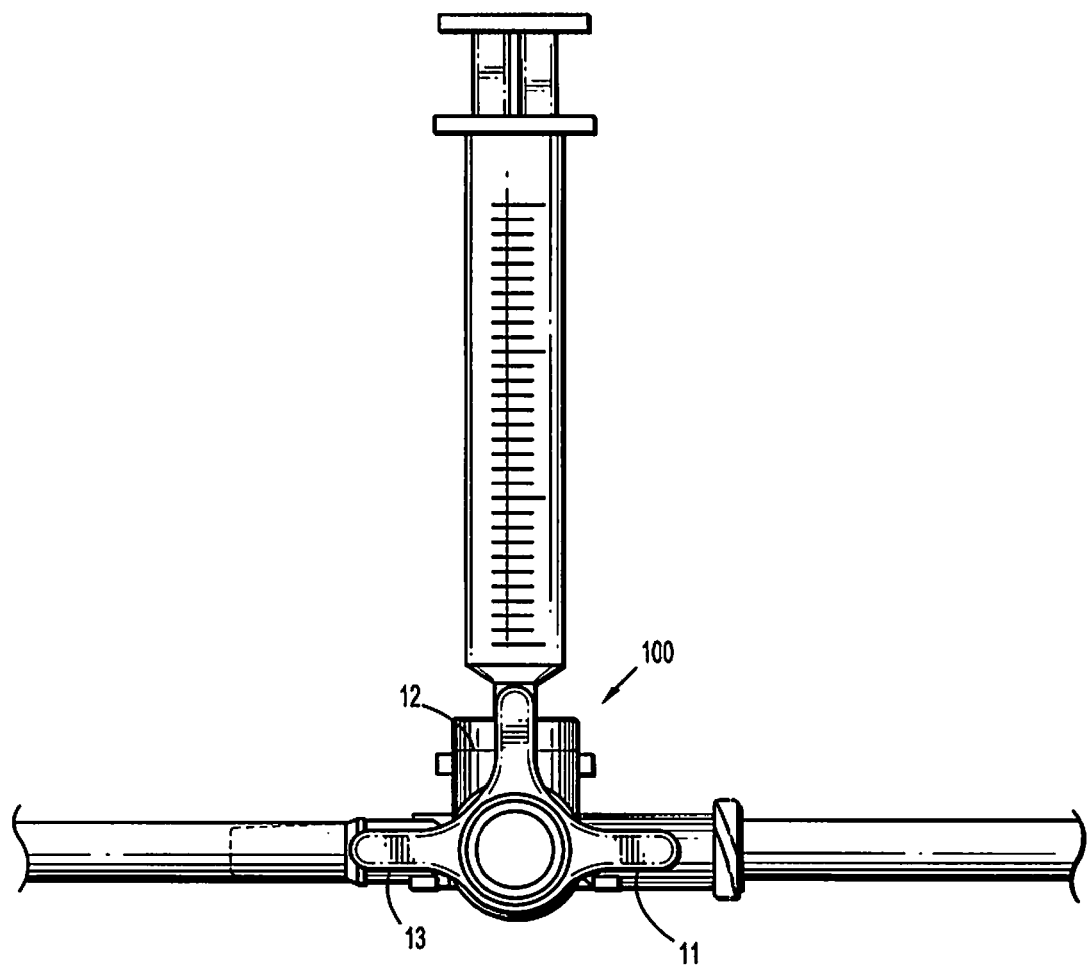
FIG. 11 shows a state in which the stopcock for medical treatment of the embodiment of the present invention is connected to a tube for medical treatment and a syringe is inserted into it.

With actual use of the three way stopcock 100 of this embodiment with the above mentioned constitution, as shown in FIG. 11, tubes for medical treatment and a syringe are mounted in the branch tubes. In this embodiment, tubes for medical treatment are mounted in the first branch tube 11 and the second branch tube 12. The syringe is mounted in the third branch tube 13 such that its Luer part is inserted into the slit 14a of the seal member 14. In this case, the flow channel flowing from the first branch flow channel 11a in the first channel tube 11 to the second branch flow channel 12a in the second branch tube 12 is assumed to be the main flow channel. Also, the flow channel flowing from the third branch flow channel 13a of the third branch tube 13 joins at an intermediate point of the main flow channel and becomes a mixture injection channel for mixing and injecting liquid medicine into the main flow channel. Therefore, the first branch flow channel 11a is a port at the inflow of the main flow channel, the second branch flow channel 12a is a port at the outflow of the main flow channel, and the third branch flow channel 13a is a port at the inflow of the mixture injection channel.

Also, the Luer part of the syringe mounted in the third branch tube 13 faces the axial position of the part in which the first channel section 21 of the valve 20 is formed. Therefore, the first channel section 21 opens directly under the Luer part, and the liquid from the Luer part flows into the first channel section 21. Also, if the axial channel 22b of the second channel section 22 opens directly under the Luer part, the liquid flows into the axial channel 22b.

Figure 12A:
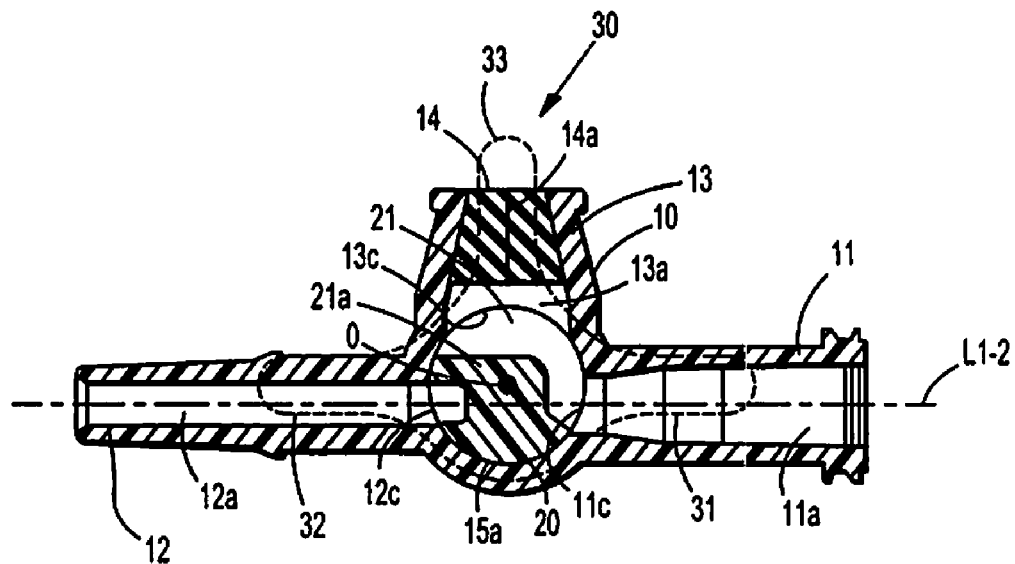
FIG. 12(a) is a cross-section of the stopcock illustrating the state of the first channel section in the valve when a main flow channel and a mixture injection channel communicate.
Figure 12B:
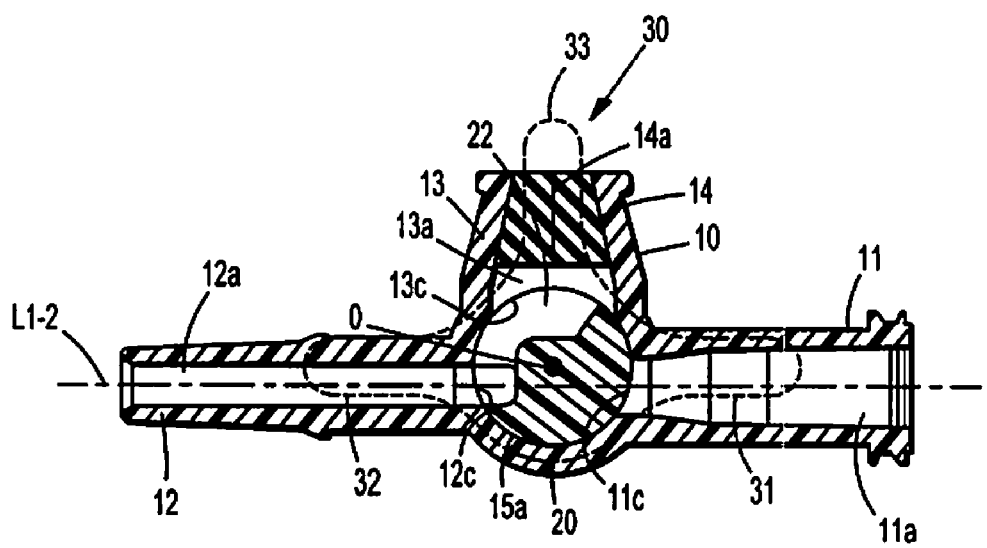
FIG. 12(b) is a cross-section of the stopcock illustrating the state of the second channel section in the valve when a main flow channel and a mixture injection channel communicate.

Next, the flow of liquid medicine using the three way stopcock 100 of this embodiment is explained. First, a state is explained in which the first branch flow channel 11a, second branch flow channel 12a, and third branch flow channel 13a communicate, and the flow of the mixture injection channel joins the flow of the main flow channel. FIGS. 12(a) and 12(b) show the arrangement of the main body 10, valve 20, and grip part 30 in this state. As shown in the figures, the first arm part 31 of the grip part 30 is positioned along the first branch tube 11, the second arm part 32 is positioned along the second branch tube 12, and the third arm part 33 is positioned along the third branch tube 13.

In this arrangement, as shown in FIG. 12(a), the first channel section 21 formed in the valve 20 is an area from the upper left side to the lower right side in the figure, that is, if indicated by the hand direction of a clock, an area from the direction of about 10 o'clock to the direction of 4 o'clock, and it is open to the outside. Also, in the state shown in the figure, the first branch flow channel 11a communicates with the cylindrical space 15a where the valve 20 is arranged from the right side in the figure. Here, as mentioned above, since the rotation center (point O in the figure) of the valve 20 is offset upward with respect to the flow channel axis L1 2 in the figure, the first inner opening part 11c of the first branch flow channel 1 a faces the valve 20 from the right side to slightly below the right side in the figure, that is, if indicated by the hand direction of a clock, from the direction of 3 o'clock to the direction of 4 o'clock. At the face of the first inner opening part 11c, since the first channel section 21 formed in the valve 20 is open, the first branch flow channel 11a communicates with the first channel section 21 from the direction of 3 4 o'clock.

Also, in the state shown in the figure, the third branch flow channel 13a communicates with the cylindrical space 15a, and the third inner opening part 13c of the third branch flow channel 13a faces the valve 20 from the upper left side to the upper right side in the figure, that is, if indicated by the hand direction of a clock, from the direction of 10 o'clock to the direction of 2 o'clock. At the face of the third inner opening part 13c, since the first channel section 21 is open, the third branch flow channel 13a communicates with the first channel section 21 from the direction of 10 2 o'clock. Therefore, in this state, the first branch flow channel 11a communicates with the third branch flow channel 13a via the first channel section 21.

In the state shown in the figure, the second branch flow section 12a communicates with the cylindrical space 15a from the left side in the figure, and as mentioned above, since the rotation center O of the valve 20 is offset to the upper side in the figure with respect to the flow channel axis L1 2, the second inner opening part 12c of the second branch flow channel 12a faces the valve 20 from the lower left side to the left side in the figure, that is, if indicated by the hand direction of a clock, in the direction 8 9 o'clock. However, the first channel section 21 is open outward only in the area from the upper left side to the lower right side of the valve 20 in the figure, that is, if indicated by the hand direction of a clock, in the area from the direction of 10 o'clock to the direction of 4 o'clock, and is not open in the direction of 8 9 o'clock. Therefore, the second branch flow channel 12a does not directly communicate with the first channel section 21.

Also, as shown in FIG. 12(b), the second channel section 22 formed in the valve 20 is opened outward in the area from the left side to the upper right side in the figure, that is, if indicated by the hand direction of a clock, in the area from the direction of 9 o'clock to the direction of 1 o'clock. In contrast, the second inner opening part 12c of the second branch flow channel 12a faces the valve 20 from the lower left side to the left side in the figure, that is, if indicated by the hand direction of a clock, in the direction of 8 9 o'clock. At the face of the second inner opening part 12c, since the second channel section 22 is open, the second branch flow channel 12a communicates with the second channel section 22 from the direction of 9 o'clock.

Also, the third inner opening part 13c of the third branch flow channel 13a faces the valve 20 from the upper left side to the upper right side in the figure, that is, if indicated by the hand direction of a clock, from the direction of about 10 o'clock to the direction of 2 o'clock. At the face of the third inner opening part 13c, there is a part in which the second channel section 22 is opened. Therefore, the third branch flow channel 13a communicates with the second channel section 22 from the direction of 10 1 o'clock. Therefore, in this state, the third branch flow channel 13a communicates with the second branch flow channel 12a via the second channel section 22.

On the other hand, the first inner opening part 11c of the first branch flow channel 11 a faces the valve 20 from the right side to slightly below the right side in the figure, that is, if indicated by the hand direction of a clock, in the direction of 3 4 o'clock. However, the second channel section 22 is open only in the area from the left side to the upper right side of the valve 20 in the figure, that is, if indicated by the hand direction of a clock, in the area from the direction of 9 o'clock to the direction of 1 o'clock and is not open in the direction of 3 4 o'clock. Therefore, the first branch flow channel 11a does not directly communicate with the second channel section 22.

In the above mentioned state, liquid medicine flows from the tube for medical treatment connected to the first branch tube 11. Thus, the liquid medicine flows from the tube for medical treatment to the first branch flow channel 11a in the first branch tube 11. Then, the liquid medicine flows from the first branch flow channel 11a to the first channel section 21 formed in the valve 20. Also, in this state, since the first channel section 21 communicates with the third branch flow channel 13a, the liquid medicine flows in the third branch flow channel 13a from the first channel 21.

The third branch flow channel 13a also communicates with the second channel section 22. Therefore, the liquid medicine introduced into the third branch flow channel 13a is further introduced into the second channel section 22. Since the second channel section 22 also communicates with the second branch flow channel 12a, the liquid medicine introduced into the second channel section 22 from the third branch flow channel 13a flows in the second branch flow channel 12a. Then, the liquid medicine is sent to the tube for medical treatment connected to the second branch tube 12. Thus, the flow by the route of the first branch flow channel 11a—first channel section 21—third branch flow channel 13a—second channel section 22 second branch flow channel 12a follows the route of the main flow channel.

As explained above, the first channel section 21 formed in the valve 20 is hindered from communicating with the second channel section 22 in the valve 20 by the partition part 20a. Therefore, liquid medicine introduced into the first channel section 21 from the first branch flow channel 11a cannot be directly introduced into the second channel section 22. For this reason, the liquid medicine is first introduced into the third branch flow channel 13a from the first channel section 21, passes through the third branch flow channel 13a, and flows into the second channel section 22. In other words, the third branch flow channel 13a is also utilized as part of the main flow channel.

In the prior art, the space in the third branch flow channel 13a as a mixture injection channel is dead space, irrelevant to the flow of the main flow channel, and is a cause for the retention of liquid medicine or air bubbles. In contrast, in this embodiment, the space of the third branch flow channel 13a is also utilized for the main flow channel. Therefore, compared to the prior art, the dead space can be reduced, and the retention of air bubbles and liquid medicine can be reduced. Also, if air bubbles remain in the third branch flow channel 13a, the air bubbles can be pushed out by the flow of the main flow channel. Therefore, in an initial priming operation, air bubbles in the third branch flow channel 13a can be pushed out, and a separate air bubble discharge operation may not be required. Thus, the workability is improved.

In a state in which liquid medicine flows in the main flow channel, if another liquid medicine is mixed and injected from the third branch flow channel, the liquid is fed into the third branch flow channel 13a from the Luer part of a syringe inserted into the slit 14a of the seal member 14. The liquid medicine fed into the third branch flow channel 13a joins the flow of the main flow channel, is carried in the main flow channel, and flows in the second channel section 22 and the second branch flow channel 12a. Then, the liquid medicine is sent to the tube for medical treatment connected to the second branch flow channel 12a. Here, since the third branch flow channel 13a is part of the route of the main flow channel, the liquid medicine in the third branch flow channel 13a flows via the main flow channel and is prevented from remaining in it.

Figure 13A:
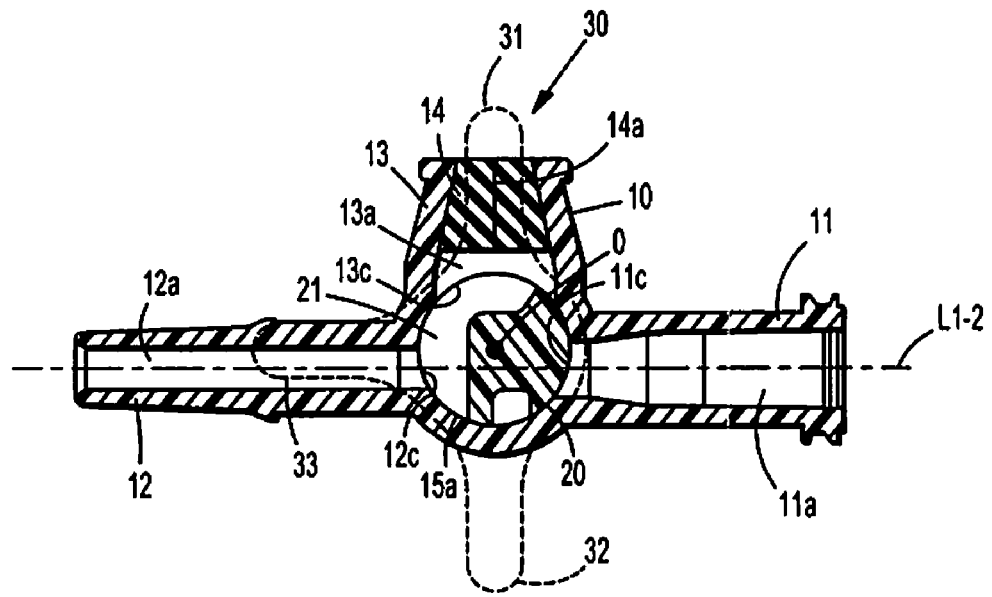
FIG. 13(a) is a cross-section of the stopcock illustrating the state of the first channel section in the valve when the flow of the main flow channel is cut off and only the mixture injection channel communicates.
Figure 13B:
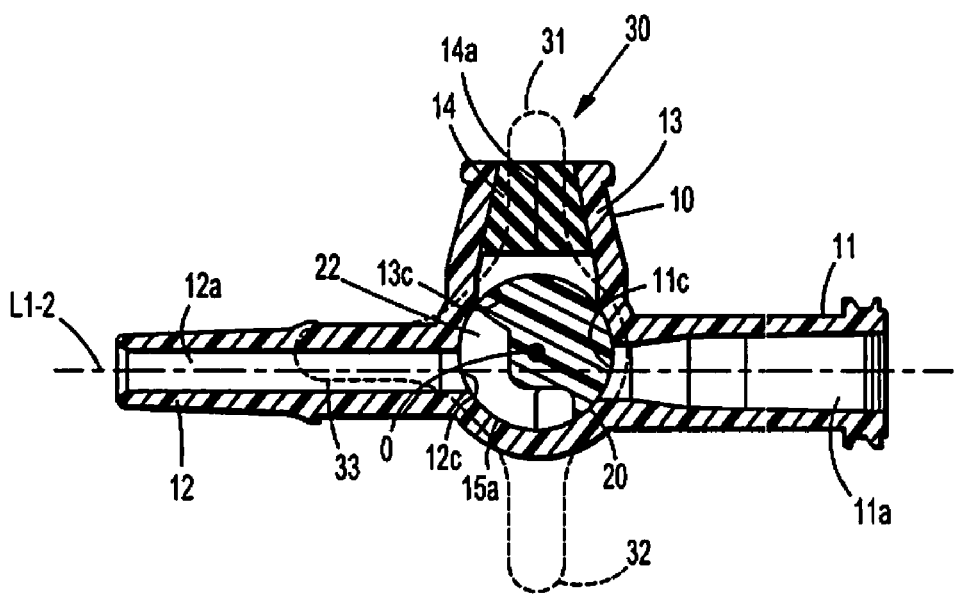
FIG. 13(b) is a cross-section of the stopcock illustrating the state of the second channel section in the valve when the flow of the main flow channel is cut off and only the mixture injection channel communicates.

Next, the case where the second branch flow channel 12a and the third branch flow channel 13a communicate, the communication of the first branch flow channel 11a and the second branch flow channel 12a is cut off, and the flow from only the mixture injection channel is supplied to the second branch flow channel 12a is explained. FIGS. 13(a) and 13(b) show the arrangement relationship among the main body 10, valve 20, and grip part 30 in this state. As shown in the figures, the first arm part 31 of the grip part 30 is positioned along the third branch flow channel 13, and the third arm part 33 is positioned along the second branch tube 12. This arrangement state occurs when the arrangement state of the grip part 30 in FIGS. 12(a) and (b) is rotated by 90° to the left (counterclockwise rotating direction). Therefore, the first channel part 21 and the second channel part 22 formed in the valve 20 are also rotated by 90° to the left (counterclockwise rotating direction) from the state shown in FIG. 12.

As shown in FIG. 13(a), the first channel section 21 formed in the valve 20 opens outward in the area from the lower left side to the upper right side in the figure, that is, if indicated by the hand direction of a clock, in the area from the direction of 7 o'clock to the direction of 1 o'clock. In contrast, the second inner opening part 12c of the second branch flow channel 12a faces the valve 20 from the lower left side to the left side in the figure, that is, if indicated by the hand direction of a clock, in the direction of 8 9 o'clock. Also, the third inner opening part 13c of the third branch flow channel 13a faces the valve 20 from the upper left side to the upper right side in the figure, that is, if indicated by the hand direction of a clock, from the direction of about 10 o'clock to the direction of 2 o'clock. At the faces of these second and third inner opening parts 12c and 13c, the first channel section 21 is opened. Therefore, the third branch flow channel 13a communicates with the second branch flow channel 12a via the first channel section 21.

On the other hand, the first inner opening part 11c of the first branch flow channel 11a faces the valve 20 from the right side to slightly below the right side in the figure, that is, if indicated by the hand direction of a clock, in the direction of 3 4 o'clock. However, the first channel section 21 does not open in this direction. Therefore, the first branch flow channel 11a does not directly communicate with the first channel section 21.

Also, as shown in FIG. 13(b), the second channel section 22 formed in the valve 20 opens outward in the area from the lower side to the upper left side in the figure, that is, if indicated by the hand direction of a clock, in the area from the direction of 6 o'clock to the direction of 10 o'clock. In contrast, the first inner opening part 11c of the first branch flow channel 11a faces the valve 20 from the right side to slightly below the right side in the figure, that is, if indicated by the hand direction of a clock, in the direction of 3 4 o'clock. Also, the third inner opening part 13c of the third branch flow channel 13a faces the valve 20 from the upper left side to the upper right side in the figure, that is, if indicated by the hand direction of a clock, from the direction of about 10 o'clock to the direction of 2 o'clock. However, the second channel section 22 does not open in the direction opposite the first inner opening part 11c and the third inner opening part 13c. Therefore, the first branch flow channel 11a and the third branch flow channel 13a do not directly communicate with the second channel section 22.

On the other hand, the second inner opening part 12c of the second branch flow channel 12a faces the valve 20 from the lower left side to the left side in the figure, that is, if indicated by the hand direction of a clock, in the direction of 8 9 o'clock. At the face of the second inner opening part 12c, since the second channel section 22 is open, the second branch flow channel 12a communicates with the second channel section 22 from the direction of 8 9 o'clock. However, the second channel section 22 does not communicate with the first branch flow channel 11a and the third branch flow channel 13a as mentioned above, and the second branch flow channel 12a does not communicate with the other branch flow channels via the second channel section 22.

In the above mentioned state, liquid medicine flowing from the tube for medical treatment connected to the first branch tube 11 flows in the first branch flow channel 11a, but since the first branch flow channel 11a does not communicate with the first channel section 21 and the second channel section 22 and is cut off by the outer peripheral wall of the valve 20, the liquid medicine is interrupted by this part. On the other hand, liquid medicine from the syringe connected to the third branch flow channel 13a is first introduced into the third branch flow channel 13a. Since the third branch flow channel 13a communicates with the second branch flow channel 12a via the first channel section 21, the liquid medicine flows in the second branch flow channel 12a via the first channel section 21 from the third branch flow channel 13a. Then, the liquid medicine is sent to the tube for medical treatment connected to the second branch flow channel 12a.

Thus, in the state shown in FIGS. 13(a) and (b), the flow of the main flow channel from the first branch flow channel 11a is cut off, and the flow from the third branch flow channel 13a as a mixture injection channel is introduced into the second branch flow channel 12a.

Figure 14A:
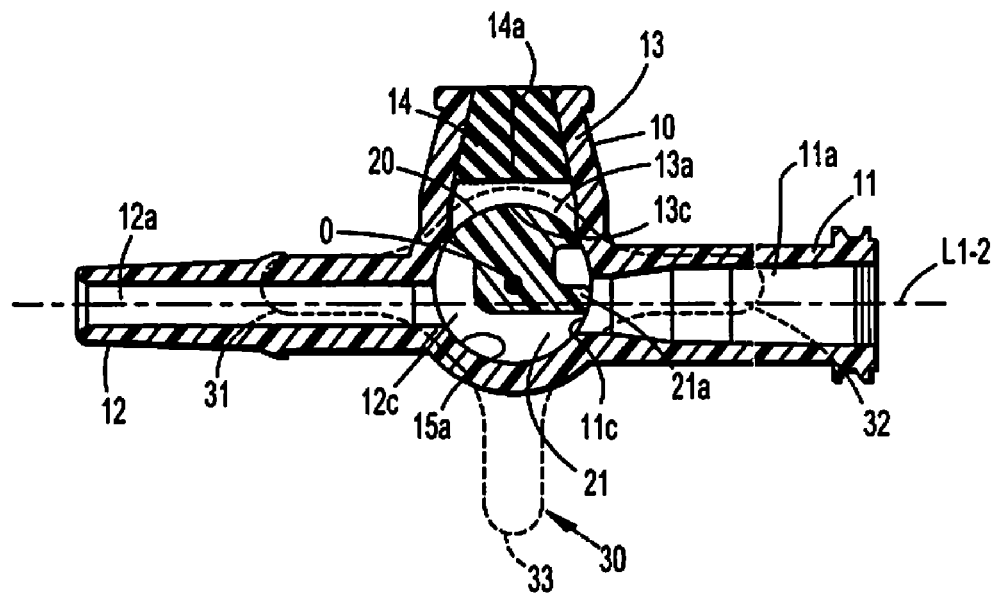
FIG. 14(a) is a cross-section of the stopcock illustrating the state of the first channel section in the valve when the flow of the mixture injection channel is cut off and only the main flow channel communicates.
Figure 14B:
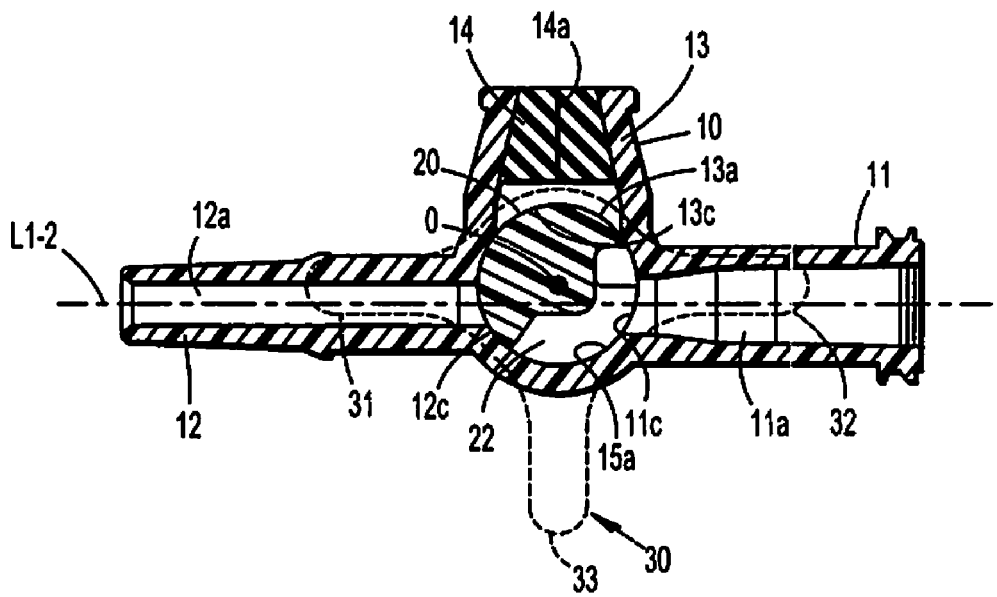
FIG. 14(b) is a cross-section of the stopcock illustrating the state of the second channel section in the valve when the flow of the mixture injection channel is cut off and only the main flow channel communicates.

Next, in the case where the first branch flow channel 11a and the second branch flow channel 12a communicate, the communication of the second branch flow channel 12a and the third branch flow channel 13a is cut off, and flow from only the main flow channel is supplied to the second branch flow channel 12a is explained. FIGS. 14(a) and 14(b) show the arrangement relationship among the main body 10, valve 20, and grip part 30 in this state. As shown in the figures, the first arm part 31 of the grip part 30 is positioned along the second branch tube 12, and the second arm part 32 is positioned along the first branch tube 11. This arrangement state occurs when the arrangement state of the grip part 30 in FIGS. 13(a) and (b) is rotated by 90° to the left (counterclockwise rotating direction). Therefore, the first channel part 21 and the second channel part 22 formed in the valve 20 are also rotated by 90° to the left (counterclockwise rotating direction) from the state shown in FIG. 13.

As shown in FIG. 14(a), the first channel section 21 formed in the valve 20 opens outward in the area from the lower right side to the upper left side in the figure, that is, if indicated by the hand direction of a clock, in the area from the direction of 4 o'clock to the direction of 10 o'clock. In contrast, the first inner opening part 11c of the first branch flow channel 11a faces the valve 20 from the right side to slightly below the right side in the figure, that is, if indicated by the hand direction of a clock, in the direction of 3 4 o'clock. At the face of the first inner opening part 11c, since the end (the end of the lower right side in the figure) of the first channel section 21 is slightly open, the first branch flow channel 11a communicates with the first channel section 21 from the direction of 4 o'clock.

Also, the second inner opening part 12c of the second branch flow channel 12a faces the valve 20 from the lower left side to the left side in the figure, that is, if indicated by the hand direction of a clock, in the direction of 8 9 o'clock. At the face of the second inner opening part 12c, since the first channel section 21 is open, the second branch flow channel 12a communicates with the first channel section 21 from the direction of 8 9 o'clock. Therefore, in this state, the first branch flow channel 11a communicates with the second branch flow channel 12a via the first channel section 21.

On the other hand, the third inner opening part 13c of the third branch flow channel 13a faces the valve 20 from the upper left side to the upper right side in the figure, that is, if indicated by the hand direction of a clock, from the direction of about 10 o'clock to the direction of 2 o'clock. However, the first channel section 21 does not open in this direction. Therefore, the third branch flow channel 13a does not directly communicate with the first channel section 21.

Also, as shown in FIG. 14(b), the second channel section 22 formed in the valve 20 opens outward in the area from the right side to the lower left side in the figure, that is, if indicated by the hand direction of a clock, in the area from the direction of 3 o'clock to the direction of 7 o'clock. On the other hand, the first inner opening part 11c of the first branch flow channel 11a faces the valve 20 from the right side to slightly below the right side in the figure, that is, if indicated by the hand direction of a clock, in the direction of 3 4 o'clock. At the face of the first inner opening part 11c, since the second channel section 22 is open, the first branch flow channel 11a communicates with the second channel section 22 from the direction of 3 4 o'clock.

In contrast, the third inner opening part 13c of the third branch flow channel 13a faces the valve 20 from the upper lower left side to the upper right side in the figure, that is, if indicated by the hand direction of a clock, from the direction of about 10 o'clock to the direction of 2 o'clock. Also, the second inner opening part 12c of the second branch flow channel 12a faces the valve 20 from the lower left side to the left side in the figure, that is, if indicated by the hand direction of a clock, in the direction of 8 9 o'clock. However, the second channel section 22 does not open in the direction opposite these opening parts 13c and 12c. Therefore, the third branch flow channel 13a and the second branch flow channel 12a do not directly communicate with the second channel section 22.

In the above mentioned state, first, liquid medicine from the tube for medical treatment connected to the first branch tube 11 flows in the first branch flow channel 11a. The first branch flow channel 11a communicates with both the first channel section 21 and the second channel section 22. However, the second channel section 22 does not communicate with the second branch flow channel 12a or the third branch flow channel 13a but forms a dead alley. Therefore, the liquid medicine in the first branch flow channel 11a flows in the first channel section 21. Since the first channel section 21 also communicates with the second branch flow channel 12a, liquid medicine introduced into the first channel section 21 flows in the second branch flow channel 12a. Then, the liquid medicine is sent to the tube for medical treatment connected to the second branch flow channel 12a.

On the other hand, the third branch flow channel 13a does not communicate with the first channel section 21 or the second channel section 22. Therefore, the flow from the third branch flow channel 13a as a mixture injection channel is cut off. Thus, when only the flow of the main flow channel from the first branch flow channel 11a is sent to the second branch flow channel 12a and the flow from the third branch flow channel 13a as a mixture injection channel is cut off, the state as shown in FIGS. 14(a) and (b) is formed.

On the other hand, the state of the first channel section 21 shown in FIG. 14(a) occurs when the valve 20 is rotated by 180° from the state of the first channel section 21 shown in FIG. 12(a). One end 21a of the first channel section 21 is positioned at the second branch flow channel 12a in the state shown in FIG. 12(a) and is positioned at the first branch flow channel 11a in the state shown in FIG. 14(a). However, in the state shown in FIG. 12(a), one end 21a of the first channel section 21 does not face the second inner opening part 12c of the second branch flow channel 12a, whereas in the state shown in FIG. 14(a), one end 21a of the first channel section 21 faces the first inner opening part 11c of the first branch flow channel 11a.

This occurs because the rotation center O of the valve 20 is offset to the upper side in FIGS. 12(a) and 14(a) with respect to the flow channel axis L1 2 of the first branch flow channel 11a and the second branch flow channel 12a. With the offset of the valve 20 as mentioned above, the first inner opening part 11c of the first branch flow channel 11a and the second inner opening part 12c of the second branch flow channel 12a face a position slightly lower than the height position of the rotation center O of the valve 20. In other words, the first inner opening part 11c of the first branch flow channel 11a faces the lower left side (if indicated by the hand direction of a clock, the direction of 8 9 o'clock) of the valve 20, and the second inner opening part 12c of the second branch flow channel 12a faces the lower right side (if indicated by the hand direction of a clock, the direction of 3 4 o'clock) of the valve 20.

In this case, in the state shown in FIG. 12(a), the first channel section 21 is formed from the upper left side to the lower right side (if indicated by the hand direction of a clock, the direction of 10 4 o'clock) of the outer periphery of the valve 20. Then, as shown in the figure, one end 21a of the first channel section 12 does not face the second inner opening part 12c of the second branch flow channel 12a. However, in the state of FIG. 14(a) in which the valve 20 is rotated by 180°, the first channel section 21 is formed from the lower right side to the upper left side (if indicated by the hand direction of a clock, the direction of 4 10 o'clock) of the outer periphery of the valve 20, so that its one end 21a slightly faces the first inner opening part 11c of the first branch flow channel 11a. For this reason, the first branch flow channel 11a communicates with the first channel section 21.

In contrast, for example, if the rotation center of the valve 20 is not offset and the rotation center of the valve 20 is positioned on the axial line of the flow channel axis L1 2, the first inner opening part 11c of the first branch flow channel 11a faces the valve 20 from the right side in FIG. 14(a), that is, if indicated by the hand direction of a clock, from the direction of 3 o'clock. However, since the first channel section 21 opens only in the direction of 4 10 o'clock, the first branch flow channel 11a does not communicate with the first channel section 21.

Thus, in the three way stopcock 100 of this embodiment, the rotation center of the valve 20 is offset with the respect to the flow channel axis (that is, the straight line that connects the center of the first inner opening part 11c and the center of the second inner opening part 12c) L1 2 of the first branch flow channel 11a and the second branch flow channel 12a. For this reason, before and after the valve 20 rotates at 180°, the arrangement state of each inner opening part 11c, 12c, and 13c and each channel section (the first channel section 21 and the second channel section 22) can differ. Utilizing this characteristic, a communication state of various branch flow channels can be realized.

Figure 15A:
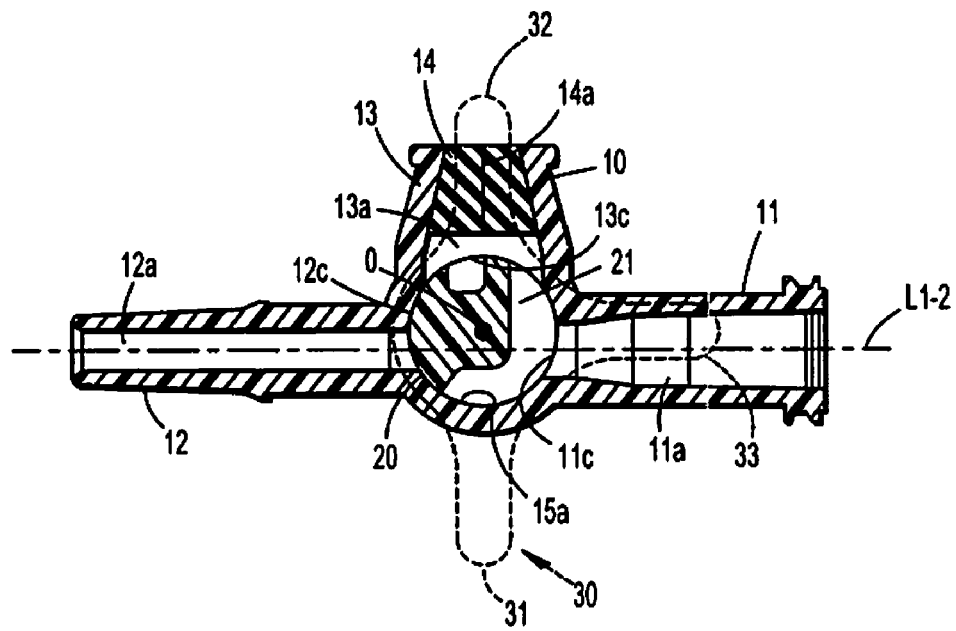
FIG. 15(a) is a cross-section of the stopcock illustrating the state of the first channel section in the valve when the flow of the main flow channel and the mixture injection channel is cut off.
Figure 15B:
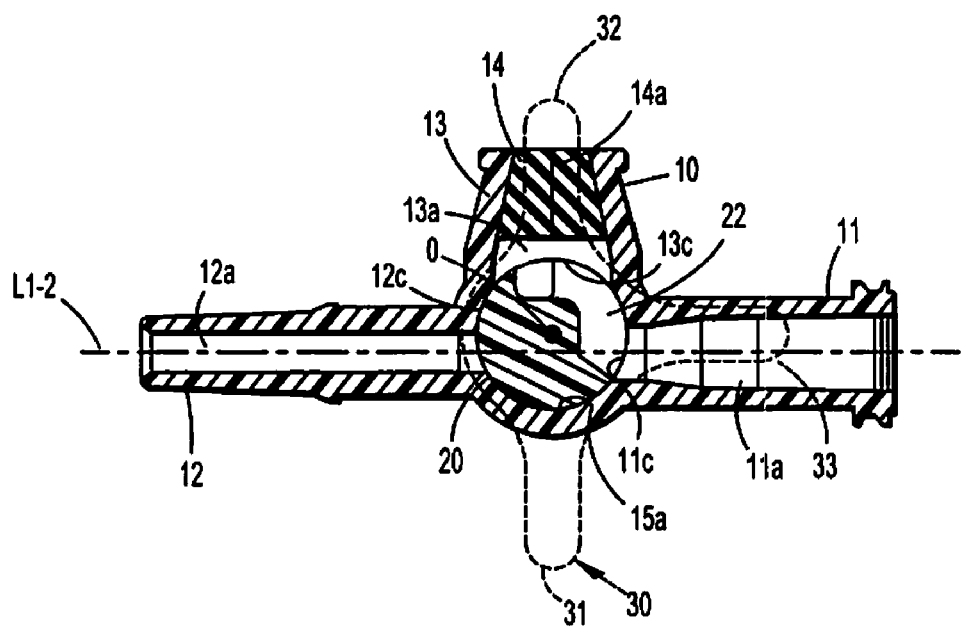
FIG. 15(b) is a cross-section of the stopcock illustrating the state of the second channel section in the valve when the flow of the main flow channel and the mixture injection channel is cut off.

Next, the case is explained where the communication of the second branch flow channel 12a and the first branch flow channel 11a and the communication of the second branch flow channel 12a and the third branch flow channel 13a are cut off and the flow supply of the main flow channel and the mixture injection channel to the second branch flow channel 12a is stopped. FIGS. 15(a) and 15(b) show the arrangement relationship among the main body 10, valve 20, and grip part 30 in this state. As shown in the figures, the second arm part 32 of the grip part 30 is positioned along the third branch tube 13, and the third arm part 33 is positioned along the first branch tube 11. This arrangement state occurs when the grip part 30 in FIGS. 14(a) and (b) is rotated by 90° to the left (counterclockwise rotating direction). Therefore, an arrangement state of the first channel part 21 and the second channel part 22 formed in the valve 20 also occurs when the state shown in FIG. 14 is rotated by 90° to the left (counterclockwise rotating direction).

As shown in FIG. 15(a), the first channel section 21 formed in the valve 20 opens outward in the area from the upper right side to the lower left side in the figure, that is, if indicated by the hand direction of a clock, in the area from the direction of 1 o'clock to the direction of 7 o'clock. In contrast, the first inner opening part 11c of the first branch flow channel 11a faces the valve 20 from the right side to the lower right side in the figure, that is, if indicated by the hand direction of a clock, in the direction of 3 4 o'clock. Also, the third inner opening part 13c of the third branch flow channel 13a faces the valve 20 from the upper left side to the upper right side in the figure, that is, if indicated by the hand direction of a clock, from the direction of about 10 o'clock to the direction of 2 o'clock. At the faces of the first and third inner opening parts 11c and 13c, the first channel section 21 is open. Therefore, the first branch flow channel 11a and the third branch flow channel 13a communicate with the first channel section 21.

On the other hand, the second inner opening part 12c of the second branch flow channel 12a faces the valve 20 from the lower left side to the left side in the figure, that is, if indicated by the hand direction of a clock, in the direction of 8 9 o'clock. However, the first channel section 21 is not open in this direction. Therefore, the second branch flow channel 12a does not communicate with the first channel section 21.

Also, as shown in FIG. 15(b), the second channel section 22 formed in the valve 20 opens outward in the area from the upper side to the lower right side in the figure, that is, if indicated by the hand direction of a clock, in the area from the direction of 12 o'clock to the direction of 4 o'clock. In contrast, the first inner opening part 11c of the first branch flow channel 11a faces the valve 20 from the right side to slightly below the right side in the figure, that is, if indicated by the hand direction of a clock, in the direction of 3 4 o'clock. Also, the third inner opening part 13c of the third branch flow channel 13a faces the valve 20 from the upper left side to the upper right side in the figure, that is, if indicated by the hand direction of a clock, from the direction of about 10 o'clock to the direction of 2 o'clock. At the faces of these first and third inner opening parts 11c and 13c, the second channel section 22 is open. Therefore, the first branch flow channel 11a and third branch flow channel 13a communicate with the second channel section 22.

On the other hand, the second inner opening part 12c of the second branch flow channel 12a faces the valve 20 from the lower left side to the left side in the figure, that is, if indicated by the hand direction of a clock, in the direction of 8 9 o'clock. However, the second channel section 22 does not open in this direction. Therefore, the second branch flow channel 12a does not communicate with the second channel section 22.

In the above mentioned state, first, liquid medicine from the tube for medical treatment connected to the first branch tube 11 flows in the first branch flow channel 11a. The first branch flow channel 11a communicates with both the first channel section 21 and the second channel section 22; however since the second branch flow channel 12a as the outflow destination does not communicate with the first channel section 21 or the second channel section 22, the first branch flow channel 11a does not communicate with the second branch flow channel 12a. Similarly, the third branch flow channel 13a communicates with both the first channel section 21 and the second channel section 22; however since the second branch flow channel 12a as the outflow destination does not communicate with the first channel section 21 or the second channel section 22, the third branch flow channel 13a does not communicate with the second branch flow channel 12a. Therefore, both the circulation of the liquid medicine from the first branch flow channel 11a as the main flow channel and the circulation of the liquid medicine from the third branch flow channel 13a as the mixture injection channel to the second branch flow channel 12a are cut off.

Here, as mentioned above, the Luer part of a syringe inserted into the third branch flow channel 13a faces the axial position of the part in which the first channel section 21 of the valve 20 is formed; however the first channel section 21 is not formed opposite the position of the Luer part. However, as shown in FIG. 15(a), the axial channel part 22b of the second channel section 22 is formed opposite and directly under the Luer part. For this reason, liquid medicine dropped or flowing down from the Luer part is reliably received by the second channel section 22. The liquid medicine received by the second channel section 22 flows from the second channel section 22 to the first branch flow channel 11 a and is mixed with the liquid medicine flowing from the first branch flow channel 11a. If the flow channel is communicated by the rotation of grip part 30, mixed liquid medicine flows in a liquid state to the branch flow channel.

Thus, the three way stopcock 100 of this embodiment can realize a state in which the main flow channel and the mixture injection channel are joined to obtain flow by rotating the valve 20 or a case where flow occurs only in the main flow channel (the case of FIGS. 12(a) and (b)), a case where flow occurs only in the mixture injection channel (the case of FIGS. 13(a) and (b)), a case where the flow of the main flow channel and the mixture injection channel is cut off (the case of FIGS. 15(a) and (b)), and a case where the flow of the mixture injection channel is cut off and flow occurs only in the main flow channel in a state in which the tubes and the syringe are connected to the mixture injection channel (the case of FIGS. 14(a) and (b)).

As explained above, in the three way stopcock 100 of this embodiment, the first channel section 21 as a first communication flow channel and the second channel section 22 as a second communication flow channel are formed in the valve 20, and the communication of the first channel section 21 and the second channel section 22 in the valve is cut off by the partition part 20a. For this reason, in the case shown in FIG. 12(a), that is, the case where the first channel section 21 communicates with both the first branch flow channel 11a and the third branch flow channel 13a, the communication with the second branch flow channel 12a is cut off, the second channel section 22 communicates with both the second branch flow channel 12a and the third branch flow channel 13a, and the communication with the first branch flow channels 11a is cut off, the flow constituting the main flow channel flows from the first branch flow channel 11a to the first channel section 21, is fed into the third branch flow channel 13a from the first channel section 21, flows from the third branch flow channel 13a to the second channel part 22, and finally arrives at the second branch flow channel 12a.

Thus, dead space in the third branch flow channel 13a can be reduced by extending the flow of the main flow channel to the third branch flow channel 13a as a mixture injection channel. Therefore, since the liquid sent from the third branch flow channel 13a and is mixed with the main flow channel and reliably sent, the retention and residence of the liquid in the third branch flow channel 13a is reduced. Furthermore, even if air bubbles remain in this part, the air bubbles are pushed out with the liquid medicine by an initial priming operation, etc. Therefore, since no separate process to remove the air bubbles is required, the workability can be satisfactorily improved.

Also, the first channel section 21 and the second channel section 22 are formed in parallel at the outer periphery of the valve 20, and channel sections 21 and 22 can be formed to approach each other. For this reason, when the third inner opening part 13c of the third branch flow channel 13a communicates with each of the first channel section 21 and the second channel section 22, the opening can be prevented from being increased more than is necessary.

Also, in this embodiment, the second channel section 22 consists of the peripheral channel part 22a formed in the peripheral direction of the valve 20 and the axial channel part 22b extending in the axial direction of the valve from an end of the peripheral channel part 22a. With the formation of the axial channel part 22b, the second channel section 22 can be formed widely in the axial direction, so that the liquid from the Luer part of the syringe inserted into the third branch flow channel 13a as shown in FIG. 15(a) can be reliably introduced into the second channel section 22.

Also, since the rotational central axis (the center O of the cylindrical space 15a) of the valve 20 is offset from the flow channel axis L1 2 (the straight line that connects the center of the first inner opening part 11c and the center of the second inner opening part 12c), the arrangement state of the inner opening parts 11c, 12c, and 13c of each branch flow channel and the first channel section 21 and the second channel section 22 of the valve 20 can differ. Utilizing this characteristic, the communication of various flow channels can be realized by rotating the valve 20.

Figure 16A:
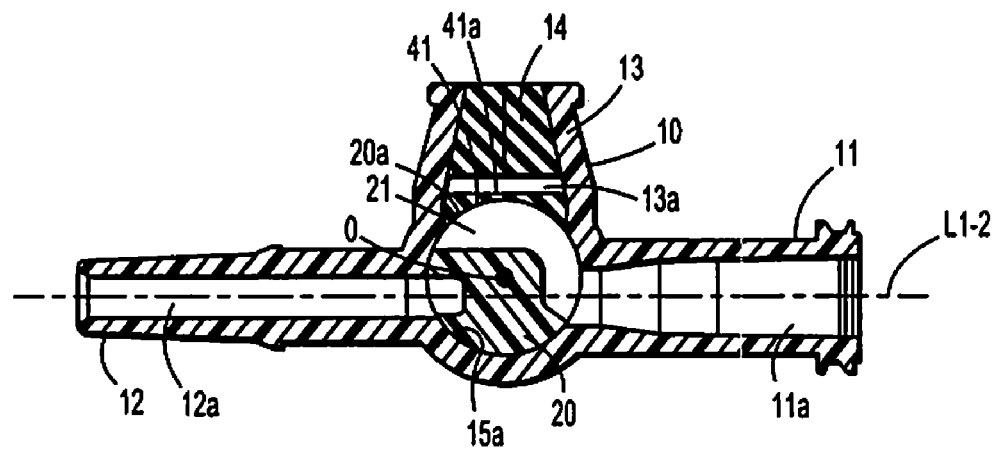
FIG. 16(a) is a cross section of another embodiment of a stopcock illustrating an arrangement state of the first channel section in the valve.
Figure 16B:
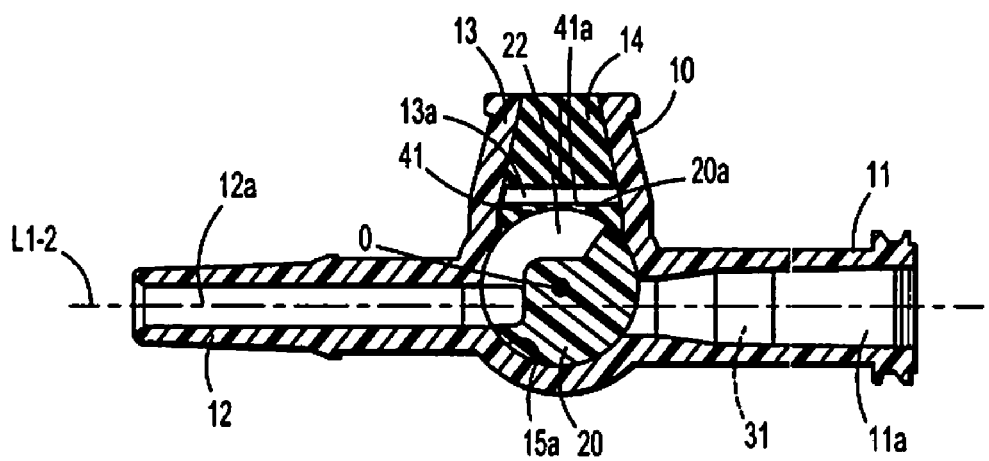
FIG. 16(b) is a cross section of the stopcock illustrating an arrangement state of the second channel section in the valve.

FIG. 16 is a cross section showing a three way stopcock as another embodiment of the present invention and corresponds to FIG. 12 in the above mentioned embodiment. The three way stopcock of this embodiment is characterized by installing a second partition part 41 in the third branch flow channel 13a in addition to the constitution of the three way stopcock in the above mentioned embodiment. The second partition part 41, as shown in FIGS. 16(a) and (b), is formed at the inner wall of the main body 10 in the third branch flow channel 13a. Also, the second partition part 41 is formed at a position to be liquid tightly contactable with the partition part 20a formed between the first channel section 21 and the second channel section 22 of the valve 20, and if the valve 20 is rotated to form the state shown in the figure, the second partition part is arranged right at the upper part of the partition part 20a in the figure. Then, the second partition part extends in the axial direction of the third branch flow channel 13a from the partition part 20a as if that the partition part 20a were raised.

For this reason, in order for the liquid flowing in the first channel section 21 from the first branch flow channel 11a to be introduced into the second channel section 22 via the third branch flow channel 13a, it must climb over the second partition part 41 in addition to the partition part 20a. Here, since the second partition part 41 extends in the axial direction of the third branch flow channel 13a, when the liquid to be introduced into the second channel section 22 from the first channel section 21 passes through the third branch flow channel 13a, the flow channel section area is reduced as shown in the figure by the second partition part 41. With the reduction of the flow channel section area, the liquid overflowing from the first channel section 21 passes through almost the entire flow channel cross section of the third branch flow channel 13a and flows into the second channel section 22. Thus, the retention of liquid and air bubbles in the third branch flow channel 13a can be reliably prevented.

Also, as can be seen from the figure, a tip surface 41a in the extending direction of the second partition part 41 is formed flatly as a plane perpendicular to the flow channel axis of the third branch flow channel 13a. For this reason, since the liquid that overflows from the first channel section 21 and flows in the third branch flow channel 13a uniformly overflows from the tip surface 41a of the second partition part 41, it uniformly flows in the third branch flow channel 13a. For this reason, the retention of liquid and air bubbles in the third branch flow channel 13a can be more reliably prevented.

At one embodiment of the present invention provides a stopcock for medical treatment that can satisfactorily prevent the retention of liquid and air bubbles by reducing the dead space in a branch flow channel of the main body.

In order to achieve the above mentioned objective, a stopcock for medical treatment of at least one embodiment of the present invention equipped with a tubular part having an inner wall, a main body consisting of a first branch flow channel that has a first opening part opening in the above mentioned inner wall and formed from the first opening part toward the outside of the above mentioned tubular part, a second branch flow channel that has a second opening part opening in the above mentioned inner wall and formed from the second opening part toward the outside of the above mentioned tubular part, and a third branch flow channel that has a third opening part opening in the above mentioned inner wall and formed from the third opening part toward the outside of the above mentioned tubular part, and a valve that is mounted at the inner periphery of the above mentioned tubular part, can be rotated around the axis of the above mentioned tubular part, and switches the communication and the cut off of the above mentioned first branch flow channel, the above mentioned second branch flow channel, and the above mentioned third branch flow channel by rotating, is characterized by the fact that the above mentioned valve is provided with a first communication flow channel that can communicate with the above mentioned first branch flow channel and the above mentioned third branch flow channel and a second communication flow channel that can communicate with both the second branch flow channel and the above mentioned third branch flow channel and can adopt a state in which the communication with the above mentioned first branch flow channel is cut off when the above mentioned first communication flow channel communicates with both the above mentioned first branch flow channel and the above mentioned third branch flow channel while communication with the above mentioned second branch flow channel is cut off; and the communication in the above mentioned valve is cut off in the above mentioned first communication flow channel and the above mentioned second communication channel.

In the stopcock for medical treatment of at least one embodiment of the present invention with the above mentioned constitution, if the first communication flow channel formed in the valve communicates with both the first branch flow channel and the third branch flow channel formed in the main body and does not communicate with the second branch flow channel, if a liquid such as liquid medicine is fed from the first branch flow channel, the liquid flows in the first communication flow channel from the first branch flow channel. At that time, since the first communication flow channel communicates with the third branch flow channel and does not communicate with the second branch flow channel, the liquid in the first communication flow channel is fed into the third branch flow channel.

On the other hand, when the first communication flow channel communicates with both the first branch flow channel and the third branch flow channel and does not communicate with the second branch flow channel, the second communication flow channel has communication with both the second branch flow channel and the third branch flow channel, and the communication with the first branch flow channel is cut off. For this reason, liquid flowing in the third branch flow channel from the first communication flow channel can flow in the second communication flow channel from the third branch flow channel. Thus, liquid flowing in the second communication flow channel further flows in the second branch flow channel. At that time, since the communication of the second communication flow channel and the first branch flow channel is cut off, the liquid in the first branch flow channel does not directly flow into the second communication flow channel, nor does the liquid of the second communication flow channel flow backward into the first branch flow channel.

Therefore, the liquid from the first branch flow channel passes through a route of the first branch flow channel—first communication flow channel—third branch flow channel—second communication flow channel—second branch flow channel and finally the second branch flow channel. If this series of flow channels is a main flow channel, the third branch flow channel is a mixture injection channel joined at an intermediate point to the main flow channel and constitutes part of the route of the flow of the main flow channel. Thus, the dead space in the third branch flow channel as a mixture injection channel can be reduced by extending the route of flow of the main flow channel to the third branch flow channel as a mixture injection channel. Therefore, since the liquid sent from the third branch flow channel is mixed in the main flow channel and reliably sent, the retention and residence of the liquid in the third branch flow channel is reduced.

Furthermore, even if air bubbles remain in this part, the air bubbles are pushed out with the liquid medicine by priming, etc. Therefore, since an operation to remove the air bubbles is not separately required, the workability can be satisfactorily improved. Also, the "priming" is a pretreatment, and in the present invention, it is a treatment that fills the flow channel space in this tube for medical treatment with a liquid to be sent before sending the liquid to a human body, etc.

In the above mentioned at least one embodiment of the invention, "the communication in the valve is cut off" means that the first communication flow channel and the second communication flow channel formed in the valve communicate without passing through the first branch flow channel, the second branch flow channel, and the third branch flow channel. For example, if the first communication flow channel and the second communication flow channel can communicate via a bypass circuit, etc., formed in the valve, without passing through each branch flow channel, communication in the valve is not said to be cut off. On the other hand, as explained in detail in embodiments that will be mentioned later, if the first communication flow channel communicates with the second communication flow channel via any of the branch flow channels, it can be said that communication in the valve is cut off.

Also, at the end opposite the above mentioned third opening part of the above mentioned three branch flow channel, ordinarily closed type valve members are mounted, and the third branch flow channel is closed by these valve members in an ordinary case. As three way stopcocks, there is an open three way stopcock in which the flow channel as a mixture injection channel communicates with the outside when the mixture is not injected and a closed three way stopcock in which the flow channel as a mixture injection channel is closed and cut off from the outside when the mixture is not injected. In the present invention, since the flow of only the main flow channel also passes through the third branch flow channel as a mixture injection channel, the liquid leaks to the outside from the third branch flow channel (mixture injection channel) in an open three way stopcock, so the liquid is unlikely to be to be properly transported. Therefore, if a three way stopcock in which the third branch flow channel is ordinarily closed by the ordinarily closed valve members is applied to the present invention, the above mentioned leakage is not likely to result, so the liquid can be reliably transported.

Also, the above mentioned first branch tube, the above mentioned second branch tube, and the above mentioned third branch tube may be respectively mounted at an interval of 90° in the peripheral direction of the above mentioned tubular part. With mounting in this manner, when the first branch tube and the second branch tube are arranged horizontally, the third branch tube can be directed upward, so that a syringe can be easily inserted into the third branch tube.

Also, a partition part may be formed in the above mentioned valve to hinder the communication of the above mentioned first communication flow channel and the above mentioned second communication flow channel in the valve. With this partition part, since communication in the valve of the first communication flow channel and the second communication flow channel is cut off, the liquid from the first communication flow channel is introduced into the third branch flow channel. Therefore, a route of the first communication flow channel—third branch flow channel—second communication flow channel can be formed by a simple constitution.

Also, the above mentioned first communication flow channel may be a first channel section formed in the peripheral direction at the outer periphery of the above mentioned valve, and the above mentioned second communication flow channel may be a second channel section formed in the peripheral direction at the outer periphery of the above mentioned valve such that it is parallel with the above mentioned first channel section. With the formation of the first communication flow channel and the second communication flow channel as channel sections at the outer periphery of the above mentioned valve, complicated processing such as the installation of flow channels that penetrate through the valve is not required, and the first communication flow channel and the second communication flow channel can be formed by simple processing.

Also, another stopcock for medical treatment of at least one embodiment of the present invention equipped with a tubular part having an inner wall, a main body consisting of a first branch flow channel that has a first opening part opening in the above mentioned inner wall and formed from the first opening part toward the outside of the above mentioned tubular part, a second branch flow channel that has a second opening part opening in the above mentioned inner wall and formed from the second opening part toward the outside of the above mentioned tubular part, and a third branch flow channel that has a third opening part opening in the above mentioned inner wall and formed from the third opening part toward the outside of the above mentioned tubular part, and a valve that is mounted at the inner periphery of the above mentioned tubular part, can be rotated round the axis of the above mentioned tubular part, and switches the communication and the cut off of the above mentioned first branch flow channel, the above mentioned second branch flow channel, and the above mentioned third branch flow channel by rotating, is characterized by the fact that the above mentioned valve is provided with a first channel section formed in the peripheral direction at the outer periphery of the above mentioned valve so that the above mentioned first branch flow channel and the above mentioned third branch flow channel can communicate with each other, a second channel section formed parallel to the above mentioned first channel section in the peripheral direction at the outer periphery of the above mentioned valve so that the above mentioned second branch flow channel and the above mentioned third branch flow channel can communicate with each other, and a partition part formed between the above mentioned first channel section and the above mentioned second channel section to cut off the communication of the above mentioned first channel section and the above mentioned second channel section in the above mentioned valve.

In the stopcock for medical treatment of at least one embodiment of the present invention with this constitution, the first branch flow channel and the third branch flow channel communicate via the first channel section formed in the valve. Also, the second branch flow channel and the third branch flow channel communicate via the second channel section formed in the valve. Here, the communication in the valve of the first channel section and the second channel section is cut off by the partition part. Therefore, when the first channel section communicates with the first branch flow channel and the third branch flow channel and does not communicate with the second branch flow channel, if the second channel section communicates with the second branch flow channel and the third branch flow channel and does not communicate with the first branch flow channel, the liquid such as liquid medicine fed from the first branch flow channel flows in the first channel section from the first branch flow channel, flows in the third branch flow channel from the first channel section, flows in the second channel section from the third branch flow channel, and finally flows in the second branch flow channel.

Therefore, the liquid from the first branch flow channel passes through a route of the first branch flow channel—first channel section—third branch flow channel—second channel section—second branch flow channel and finally flows in the second branch flow channel. If this series of flow channels is a main flow channel, the third branch flow channel is a mixture injection channel joined at an intermediate point to the main flow channel and constitutes part of the route of the flow of the main flow channel. Thus, dead space in the third branch flow channel can be reduced by extending the route of flow of the main flow channel to the third branch flow channel as a mixture injection channel. Therefore, since the liquid being sent from the third branch flow channel is mixed in the main flow channel and reliably sent, the retention and residence of the liquid in the third branch flow channel is reduced. Furthermore, even if air bubbles remain in this part, the air bubbles are pushed out by the liquid medicine by priming, etc. Therefore, since a separate operation for removing the air bubbles is not required, the workability can be satisfactorily improved.

Also, an axial channel section extending in the axial direction of the valve may be connected to at least one of the first channel section and the second channel section. With the formation of the axial channel section, the liquid flowing from each branch flow channel can be reliably introduced into the first channel section and/or the second channel section. Especially if the third branch flow channel is a mixture injection channel and the liquid is dropped or flows down from the third branch flow channel, if the axial position of the flow channel of the liquid being dropped or flowing down from the third branch flow channel and the channel section formed in the valve are offset, sufficient liquid cannot be introduced into the channel section. As for this problem, the liquid can be more reliably introduced into the channel section if the axial channel section forms a wide channel in the axial direction.

Furthermore, according to this constitution, with the formation of the axial channel, the first channel section and the second channel section can also be installed so that they match the axial position of the valve. If two channel sections are formed in this manner, the flow channel axis of the first branch flow channel communicating with the first channel section and that of the second branch flow channel communicating with the second channel section can be matched, so that the first branch flow channel and the second branch flow channel can be formed in a straight line.

Also, the rotational central axis of the valve may be offset from a straight line that connects the center of the above mentioned first opening part and the center of the above mentioned second opening part. In this case, the arrangement of the first opening part, the second opening part, the first communication flow channel (first channel section) and the second communication flow channel (second channel section) formed in the valve can differ after rotating by 180°. Utilizing this arrangement, the communication state of various flow channels can be realized by rotating. For example, at one rotating position of the valve, the first branch flow channel and the second branch flow channel communicate via the first and second communication flow channels (for example, the state of FIG. 12(a) explained in embodiments that will be mentioned later). On the other hand, if the valve is rotated by 180° from this position, the first branch flow channel and the second branch flow channel can communicate only by one communication channel (for example, the state of FIG. 14(a) explained above and shown in the illustrated embodiments).

Also, a second partition part arranged in a liquid tight contactable way with the above mentioned partition part and extending from the above mentioned partition part in the axial direction of the above mentioned third branch flow channel can be installed in the above mentioned third branch flow channel. With the installation of the above mentioned second partition part, the first channel section and the second channel section are partitioned by the partition part and the second partition part. In other words, the partition part is raised in the height direction by the second partition part. Therefore, in order for the liquid in the first channel section to be introduced into the second channel part, the liquid must climb over the second partition part in addition to the partition part. Here, since the second partition part extends in the axial direction of the third branch flow channel, when the liquid to be introduced into the second channel section from the first channel section passes through third branch flow channel, the flow channel section area is reduced. With the reduction in the flow channel section area, the liquid overflowing from the first channel section passes through almost the entire flow channel cross section of the third branch flow channel and is introduced into the second channel section. Therefore, the retention of liquid and air bubbles in the third branch flow channel can be reliably prevented.

Also, in this case, the end surface in the extending direction of the second partition part is preferably formed as a plane perpendicular to the flow channel axis of the third branch flow channel. In this case, since the liquid that overflows from the first channel section and flows in the third branch flow channel uniformly overflows in the end surface direction of the second partition part, it also uniformly flows in the third branch flow channel. Therefore, the retention of liquid and air bubbles in the third branch flow channel can be more reliably prevented.

Having described embodiments of the invention in detail, it will be apparent that modifications and variations are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A medical valve device comprising:
   a main body;
   first, second and third connection ports attached to said main body; and
   a valve unit rotatable in said main body for selectably connecting said connection ports together in fluid flow communication, said valve unit being shaped to provide a first fluid flow channel and a second fluid flow channel,
   wherein said valve unit is positionable in said main body
   (1) in a first state such that said first fluid flow channel provides a fluid flow connection between said first port and said third port but not said second port and said second fluid flow channel provides a fluid flow connection between said second port and said third port but not said first port, and
   (2) in a second state such that said first flow channel provides a fluid flow connection between said third port and said second port but not said first port and no fluid flow connection is provided to said first port, and
   (3) in a third state such that said second flow channel provides a fluid flow connection between said first port and said third port but not said second port and no fluid flow connection is provided to said second port;
   wherein said first fluid flow channel and said second fluid flow channel are separated in said valve unit by a partition which is positioned for engagement with an inner wall of the main body and hinders fluid communication between said first fluid channel and said second fluid channel in said valve unit.

2. The medical valve device according to claim 1 wherein said third port includes a partition wall arranged such that in said first state, said partition wall is adjacent said partition such that fluid flow from said first flow channel to said second flow channel is diverted over said partition wall.

3. The medical valve device according to claim 1 wherein said valve unit has a substantially cylindrical form and said first and second fluid channels comprise cut-outs in said substantially cylindrical form.

4. The medical valve device according to claim 3 wherein said substantially cylindrical form has a central axis and said first fluid channel extends normal to said axis and said second fluid channel extends partially normal to said axis and partially parallel to said axis.

5. The medical valve device according to claim 1 wherein said valve unit is further positionable in a fourth state such that said first flow channel provides a fluid flow connection between said first and said second ports but not said third port and no fluid flow connection is provided to said third port.

6. A stopcock for medical treatment comprising:
   a tubular part having an inner wall;
   a main body including
   a first branch flow channel with a first opening part opening into said inner wall and formed from the first opening part toward the outside of said tubular part,
   a second branch flow channel with a second opening part opening in said inner wall and formed from the second opening part toward the outside of said tubular part, and
   a third branch flow channel with a third opening part opening in said inner wall and formed from the third opening part toward the outside of said tubular part;

a valve mounted at an inner periphery of said tubular part that can be rotated around the axis of said tubular part to switch the communication and the cut off of said first branch flow channel, said second branch flow channel, and said third branch flow channel by rotating, said valve comprising a first communication flow channel that can communicate with said first branch flow channel and said third branch flow channel, and a second communication flow channel that can communicate with both the second branch flow channel and said third branch flow channel, wherein said valve is configured to adopt a state in which said first communication flow channel communicates with both said first branch flow channel and said third branch flow channel while communication with said second branch flow channel is cut off, and wherein the communication between said first communication flow channel and said second communication flow channel is cut off in said valve by a partition part which is positioned to engage the inner wall of the tubular part to hinder communication of said first communication flow channel and said second communication flow channel in said valve.

7. The stopcock for medical treatment of claim 6, wherein said first communication flow channel is a first channel section formed along an outer periphery of said valve, and wherein said second communication flow channel is a second channel section formed along the, outer periphery of said valve such that it is parallel to said first channel section.

8. A stopcock for medical treatment comprising:
   a tubular part having an inner wall;
   a main body including a first branch flow channel with a first opening part opening in said inner wall and formed from the first opening part toward the outside of said tubular part,
   a second branch flow channel with a second opening part opening in said inner wall and formed from the second opening part toward the outside of said tubular part, and
   a third branch flow channel with a third opening part opening in said inner wall and formed from the third opening part toward the outside of said tubular part; and
   a valve mounted at an inner periphery of said tubular part, said valve being configured for rotation around the axis of said tubular part and for switching the communication and the cut off of said first branch flow channel, said second branch flow channel, and said third branch flow channel by rotating said valve, said valve comprising
   a first channel section formed along an outer periphery of said valve such that said first branch flow channel and said third branch flow channel can communicate with each other,
   a second channel section formed parallel to said first channel section along the outer periphery of said valve such that said second branch flow channel and said third branch flow channel can communicate with each other, and
   a partition part in engagement with the inner wall of the tubular part formed between said first channel section and said second channel section to cut off the communication of said first channel section and said second channel section in said valve.

9. The stopcock for medical treatment of claim 8, wherein an axial channel section extending in the axial direction of said valve is connected to at least one of said first channel section and said second channel section.

10. The stopcock for medical treatment of claim 8, wherein the rotational central axis of said valve is offset from a straight line that connects the center of said first opening part and the center of said second opening part.

11. The stopcock for medical treatment of claim 8 wherein the valve further comprises a second partition part arranged in a liquid tight contactable way with said first partition part, wherein said second partition part extends from said first partition part in the axial direction of said third branch flow channel and is installed in said third branch flow channel.

* * * * *